(12) United States Patent
Scheler et al.

(10) Patent No.: US 9,227,938 B2
(45) Date of Patent: Jan. 5, 2016

(54) PHARMACEUTICAL COMPOSITION CONTAINING CRYSTALLINE SORAFENIB TOSYLATE

(71) Applicants: Stefan Scheler, Kundl (AT); Heiko Degendorfer, Kundl (AT); Johannes Raneburger, Kundl (AT); Franz Schwarz, Kundl (AT)

(72) Inventors: Stefan Scheler, Kundl (AT); Heiko Degendorfer, Kundl (AT); Johannes Raneburger, Kundl (AT); Franz Schwarz, Kundl (AT)

(73) Assignee: SANDOZ AG, Basel (CH)

( * ) Notice: Subject to any disclaimer, the term of this patent is extended or adjusted under 35 U.S.C. 154(b) by 0 days.

(21) Appl. No.: 14/371,034

(22) PCT Filed: Jan. 23, 2013

(86) PCT No.: PCT/EP2013/051219
§ 371 (c)(1),
(2) Date: Jul. 8, 2014

(87) PCT Pub. No.: WO2013/110644
PCT Pub. Date: Aug. 1, 2013

(65) Prior Publication Data
US 2015/0080435 A1    Mar. 19, 2015

Related U.S. Application Data

(60) Provisional application No. 61/589,518, filed on Jan. 23, 2012.

(30) Foreign Application Priority Data

Jan. 23, 2012  (EP) ..................... 12152165

(51) Int. Cl.
| A61K 31/4412 | (2006.01) |
| C07D 213/81 | (2006.01) |
| A61K 9/20 | (2006.01) |
| A61K 9/00 | (2006.01) |
| A61K 47/20 | (2006.01) |

(52) U.S. Cl.
CPC ............ *C07D 213/81* (2013.01); *A61K 9/0095* (2013.01); *A61K 9/2013* (2013.01); *A61K 9/2018* (2013.01); *A61K 9/2027* (2013.01); *A61K 9/2031* (2013.01); *A61K 9/2054* (2013.01); *A61K 9/2077* (2013.01); *A61K 31/4412* (2013.01); *A61K 47/20* (2013.01)

(58) Field of Classification Search
None
See application file for complete search history.

(56) References Cited

U.S. PATENT DOCUMENTS

2008/0213374 A1    9/2008    Carty

FOREIGN PATENT DOCUMENTS

| EP | 2559431 | 2/2013 |
| WO | 2006/034797 A1 | 4/2006 |
| WO | 2006/094626 A1 | 9/2006 |
| WO | 2009/092070 A1 | 7/2009 |
| WO | 2013/023970 | 2/2013 |

OTHER PUBLICATIONS

Ahmad, "Kinase inhibition with BAY 43/9006 in renal cell carcinoma," Clinical Cancer Research, the American Association for Cancer Research, US, vol. 10, No. 18, Pt. 2, Mar. 19, 2004, pp. 6388s-6392s.
International Search Report issued in PCT/EP2013/051219, Feb. 15, 2013, pp. 1-2.
Written Opinion issued in PCT/EP2013/051219, Feb. 15, 2013, pp. 1-2.
International Preliminary Report on Patentability issued in PCT/EP2013/051219, Jul. 29, 2014, pp. 1-8.
Rowe, Handbook of Pharmaceutical Excipients, Pharnaceuitcal PRess, London, 1986, p. 139.
Third party observations in European Patent Application No. 13700919.7-1455, Sep. 22, 2015, pp. 1-4.

*Primary Examiner* — Zinna Northington Davis
(74) *Attorney, Agent, or Firm* — Jeffrey S. Melcher; Manelli Selter PLLC

(57) ABSTRACT

The present invention relates to an oral solid dosage form, in particular a tablet, comprising sorafenib tosylate polymorphic form III.

15 Claims, 4 Drawing Sheets

PHARMACEUTICAL COMPOSITION CONTAINING CRYSTALLINE SORAFENIB TOSYLATE

This application is a 371 of PCT/EP2013/051219 filed Jan. 23, 2013 which claims benefit of 61/589,518 filed Jan. 23, 2012.

SUBJECT OF THE INVENTION

The present invention relates to an oral solid dosage form comprising sorafenib tosylate form III and at least one excipient. In particular, the present invention relates to an immediate release tablet comprising said sorafenib tosylate form III, to a method for the preparation of an oral solid dosage form, preferably of the above-mentioned oral solid dosage form, to said oral solid dosage form for use in the treatment of mammalian hyper-proliferate disorders, and to the use of said sorafenib tosylate form III for the preparation of an oral solid dosage form having an increased dissolution rate.

BACKGROUND OF THE INVENTION

Sorafenib, 4-(4-{3-[4-chloro-3-(trifluoromethyl)phenyl]ureido}phenoxy)-N2-methylpyridine-2-carboxamide,

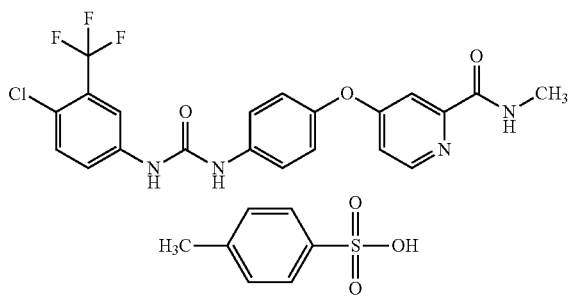

is a multikinase inhibitor. A method for its preparation is described in WO 00/42012.

Sorafenib tosylate, 4-(4-{3-[4-chloro-3-(trifluoromethyl)phenyl]ureido}phenoxy)-N2-methylpyridine-2-carboxamide 4-methylbenzenesulfonate, is a pharmaceutically active agent which can be used for the treatment of advanced renal cell carcinoma and hepatocellular carcinoma.

The preparation of different polymorphic forms of sorafenib tosylate, specifically polymorphic forms I, II, and III, is described in WO 2006/034797. In particular, WO 2006/034797 relates to the polymorphic form I, which is described as exhibiting superior stability in comparison to the other disclosed crystal forms. According to WO 2006/034797 this ensures that no undesired conversion to any other polymorph takes place as well as increased safety and quality of pharmaceutical preparations comprising polymorph I.

WO 2006/094626 relates to pharmaceutical compositions containing sorafenib. Among others, polymorphs in general, solvates, hydrates, and pharmaceutically acceptable salts of sorafenib are mentioned. As to the polymorphs, only the polymorphic form I is specifically mentioned.

WO 2009/092070 describes a processes for the preparation of the polymorphic forms I, II, and III of sorafenib tosylate, and further describes the preparation of a methanol solvate, an ethanol solvate, and a hemi-tosylate. Pharmaceutical compositions containing said compounds are only generally mentioned, and WO 2009/092070 is silent on specific pharmaceutical compositions, and no example is directed to a pharmaceutical composition.

Sorafenib tosylate is currently marketed as a coated tablet for immediate release under the trade name of Nexavar®, wherein the tablets contain the sorafenib tosylate having polymorphic form I. The tablets are packaged in expensive aluminum blisters, which are practically impermeable to water.

Additionally, in case the marketed tablets are to be dispersed in water prior to their use which becomes necessary if the respective patient in need of sorafenib tosylate struggles with swallowing problems or if the composition is to be fed to the patient via a tube, the disintegration of a tablet takes about 6 minutes. This very slow disintegration behaviour is another major drawback of the marketed tablets.

Further, the marketed tablets contain sodium lauryl sulfate which is usually used as surfactant or wetting agent. However, such a surfactant may impair both the taste and the gastric tolerability of the formulation, in particular in case the tablets have to be dispersed in water prior to their use and no taste masking is possible.

Therefore, there is a need for pharmaceutical compositions, in particular oral solid dosage forms, comprising sorafenib tosylate as active agent which allow the use of less expensive packaging materials.

Further, there is a need for pharmaceutical compositions, in particular oral solid dosage forms, comprising sorafenib tosylate as active agent which have an increased disintegration rate.

Yet further, there is need for pharmaceutical compositions, in particular oral solid dosage forms, which overcome the disadvantages of compositions containing critical surfactants such as sodium lauryl sulfate.

OBJECT AND SUMMARY OF THE INVENTION

The object of the present invention was to find an oral solid dosage form comprising sorafenib tosylate and exhibiting an improved storage stability.

It was a further object of the present invention to find pharmaceutical compositions, in particular oral solid dosage forms, comprising sorafenib tosylate as active agent, which are less affected by unfavorable storage conditions.

It was a further object of the present invention to find an oral solid dosage form comprising sorafenib tosylate having good polymorphic stability, thus avoiding undesired conversion to any other polymorph taking place during the formulation process.

It was a further object of the present invention to find an oral solid dosage form comprising sorafenib tosylate and having improved disintegration characteristics.

It was a further object of the present invention to find an oral solid dosage form comprising sorafenib tosylate and avoiding the disadvantages of the use of sodium lauryl sulfate as excipient, in particular having improved taste upon disintegration in water.

These objects as well as others which will become apparent from the ensuing description of the present invention are attained by the subject-matter of the independent claims. Some of the preferred embodiments of the present invention are defined by the subject-matter of the dependent claims.

Surprisingly, it was found that an oral solid dosage form which comprises sorafenib tosylate form III meets the above-mentioned requirements.

A further embodiment of the present invention relates to a method for the preparation of an oral solid dosage form, comprising
a) providing sorafenib tosylate form III;
b) mixing the sorafenib tosylate form III provided in a) with at least one excipient;
c) preparing the oral solid dosage form based on the mixture obtained in b).

A further embodiment of the present invention relates to said oral solid dosage form for use in the treatment of mammalian hyper-proliferate disorders.

A further embodiment of the present invention relates to the use of sorafenib tosylate form III for the preparation of an oral solid dosage form having an increased dissolution rate after packaging in a polyethylene film and storing in the dark at 40° C. at a relative humidity of 75% for a period of 14 days, compared with an identically packaged and stored oral solid dosage form comprising, instead of sorafenib tosylate form III, sorafenib tosylate form I.

A further embodiment of the present invention relates to a pharmaceutical composition comprising sorafenib tosylate form III, wherein said pharmaceutical composition is packaged in a packaging material having a moisture vapour transmission rate of at least $0.4 \text{ g m}^{-2} \text{ d}^{-1}$ as measured according to standard DIN 53122-1.

A further embodiment of the present invention relates to sorafenib tosylate form III for use in the treatment of mammalian hyper-proliferate disorders, including cancer, said disorder optionally being renal cell carcinoma or hepatocellular carcinoma, in patients in a country having an area with an Af or an Am climate, preferably an Af climate, according to the Köppen-Geiger climate classification.

Surprisingly, no conversion of the thermodynamically less stable polymorphic form III is observed during the formulation process and in particular no polymorphic form I could be detected in the formulated product.

DEFINITIONS

Figure 1:
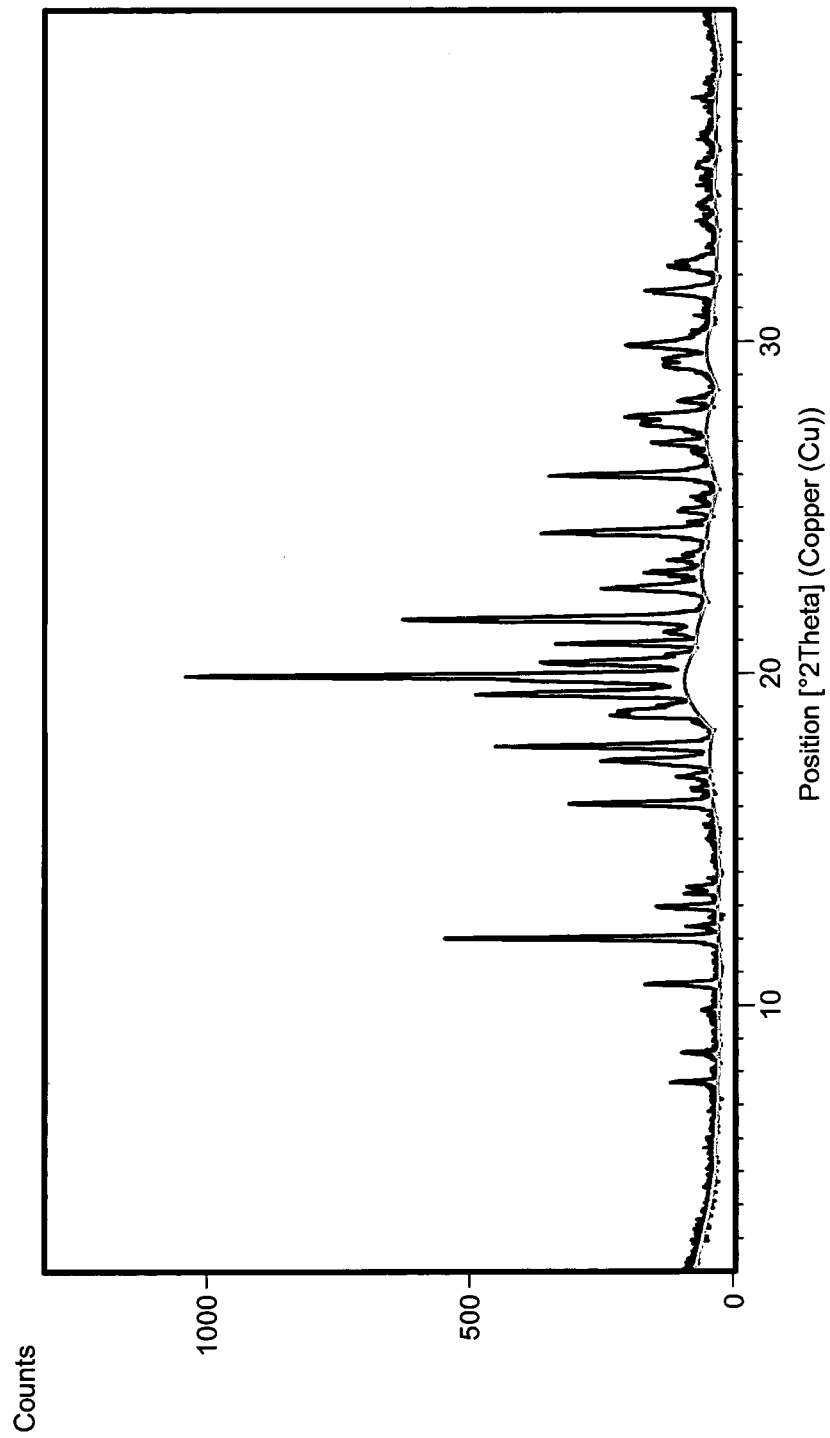
FIG. 1: XRPD pattern of sorafenib tosylate polymorphic form III analyzed according to Reference Example 1 d). On the x axis, the position [° 2 Theta] (Copper (Cu)) is shown with explicit values of 10, 20, and 30. On the y axis, the counts are shown with explicit values of 0, 500, and 1000.

The present invention illustratively described in the following may suitably be practiced in the absence of any element or elements, limitation or limitations, not specifically disclosed herein.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn to scale for illustrative purposes.

Where the term "comprising" is used in the present description and claims, it does not exclude other elements or steps. For the purposes of the present invention, the term "consisting of" is considered to be a preferred embodiment of the term "comprising". If hereinafter a group is defined to comprise at least a certain number of embodiments, this is also to be understood to disclose a group which optionally consists only of these embodiments.

Where an indefinite or definite article is used when referring to a singular noun e.g. "a" or "an", "the", this includes a plural of that noun unless something else is specifically stated.

The term "about" in the context of the present invention denotes an interval of accuracy that the person skilled in the art will understand to still ensure the technical effect of the feature in question. The term typically indicates deviation from the indicated numerical value of ±10%, and preferably ±5%.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The term "oral solid dosage form" as used herein denotes solid preparations (e.g. tablets) for oral administration each containing a single dose of one or more active substances.

In the context of the present invention, the term "Raman shift" is used according to its conventional meaning, and thus is defined as the difference between the wavenumber of the laser line used for the preparation of the Raman spectrum of a given sample, and the observed peak.

In the context of the present invention, the term "dissolution rate" relates to the percentage (weight-%) of a given oral solid dosage form which is dissolved after 15 minutes if the oral solid dosage form is subjected to dissolution conditions using an USP 2 apparatus with a stirrer speed of 75 rpm and a test temperature of 37° C. with a dissolution medium of 900 ml of a 0.1 N HCl solution comprising 1% by weight of sodium lauryl sulphate.

In the context of the present invention, the term "sugar alcohol" is used according to its conventional meaning and thus defines a hydrogenated form of carbohydrate, whose carbonyl group (aldehyde or ketone, reducing sugar) has been reduced to a primary or secondary hydroxyl group.

In the context of the present invention, the term "oligosaccharide" relates to a saccharide polymer containing a small number, typically two to ten of component sugars, also known as simple sugars (monosaccharides).

In the context of the present invention, the term "sorafenib tosylate polymorphic form III" or "sorafenib tosylate form III" relates to a crystalline sorafenib tosylate characterized by an X-ray powder diffraction pattern showing peak maxima at 2 theta/° values of 7.7±0.2, 12.0±0.2, 19.9±0.2, and 21.6±0.2, preferably at 2 theta/° values of 7.7±0.2, 10.6±0.2, 12.0±0.2, 16.1±0.2, 17.8±0.2, 19.4±0.2, 19.9±0.2, 21.6±0.2, 24.2±0.2 and 26±0.2, wherein the X-ray powder diffraction pattern is to be understood as being determined at a temperature of about 22° C. using copper-Kalpha1/2 radiation having a wavelength of 0.15419 nm, and/or characterized by a Raman spectrum showing peak maxima at Raman shift/cm$^{-1}$ values of 1715±5, 1601±5, 1334±5, 1268±5, 1033±5, and 1011±5, preferably at Raman shift/cm$^{-1}$ values of 1715±5, 1601±5, 1334±5, 1268±5, 1163±5, 1117±5, 1033±5, and 1011±5, wherein the Raman spectrum is to be understood as being determined using a laser having a wavelength of 532 nm wherein the exposure time of the sample is 2 s.

In the context of the present invention, the term "sorafenib tosylate polymorphic form I" or "sorafenib tosylate form I" relates to a crystalline sorafenib tosylate characterized by an X-ray powder diffraction pattern showing peak maxima at 2 theta/° values of 4.3±0.2, 11.0±0.2, 14.8±0.2, 17.9±0.2, 19.3±0.2, 20.5±0.2 and 20.8±0.2, 21.5±0.2, 22.9±0.2, and 24.5±0.2, wherein the X-ray powder diffraction pattern is to be understood as being determined at a temperature of about 22° C. using copper-Kalpha1/2 radiation having a wavelength of 0.15419 nm, and/or characterized by a Raman spectrum showing peak maxima at Raman shift/cm$^{-1}$ values of 1688±5, 1612±5, 1601±5, 1325±5, 1310±5, 1268±5, 1212±5, 1163±5, 1117±5, 1033±5, 1011±5, 922±5, 863±5, 825±5, 803±5, 791±5, 751±5, 685±5, and 639±5, wherein the Raman spectrum is to be understood as being determined using a laser having a wavelength of 532 nm wherein the exposure time of the sample is 2 s.

DETAILED DESCRIPTION OF THE INVENTION

The present invention relates to a pharmaceutical composition, preferably to an oral solid dosage form, in particular to an immediate release tablet.

The Oral Solid Dosage Form

In particular, the oral solid dosage form of the present invention comprises sorafenib tosylate form III.

Sorafenib tosylate form HI can be prepared by processes as described in the literature, for example in WO 2006/034797, in Example 3, on page 20, lines 1-6; or in WO 2009/092070, in Example 6, on page 16, lines 1-3, in combination with Example 5, on page 15, lines 26-31. Further, any other method for the preparation of said crystalline sorafenib tosylate is comprised by the present invention provided that said crystalline sorafenib tosylate as described above is obtained.

The oral solid dosage form of the present invention usually contains at least 50% by weight of the sorafenib tosylate form III, relative to its total content of crystalline sorafenib tosylate, preferably relative to its total content of sorafenib tosylate. More preferably, the respective content is at least 60% by weight, more preferably at least 70% by weight, more preferably at least 80% by weight. Even more preferably, said content is at least 90% by weight, more preferably at least 95% by weight such as at least 96% by weight or at least 97% by weight or at least 98% by weight or at least 99% by weight.

The oral solid dosage forms of the present invention exhibit unexpected and advantageous characteristics with respect to their susceptibility to humidity, which characteristics can be observed, e.g., if the oral dosage forms are packaged in a packaging material having a comparatively high moisture vapour transmission rate of at least 0.4 g m$^{-2}$ d$^{-1}$, preferably of at least 1 g m$^{-2}$ d$^{-1}$, more preferably of at least 2 g m$^{-2}$ d$^{-1}$, as measured according to standard DIN 53122-1, and further if the respectively packaged oral dosage forms are stored for a certain period of time, preferably for at least 2 weeks, more preferably for at least 6 months, even more preferably for at least 12 months.

Surprisingly, it was found that after such packaging and storage, the dissolution rate was significantly higher than that of the oral dosage forms presently marketed under the trade name of Nexavar® having been repackaged in comparable packaging materials. Further, it was found that the higher the amount of the sorafenib tosylate form III, contained in the oral dosage form, relative to the amount of crystalline sorafenib tosylate having a different polymorphic form, in particular relative to the amount of sorafenib tosylate form I, the better said dissolution rate after storage.

According to the present invention, the oral solid dosage forms contain at most 50% by weight, preferably at most 40% by weight, more preferably at most 30% by weight, more preferably at most 20% by weight, more preferably at most 10% by weight of a crystalline sorafenib tosylate having a polymorphic form other than the polymorphic form III. Preferably the crystalline sorafenib tosylate having a polymorphic form other than the polymorphic form III is the sorafenib tosylate form I. More preferably, said amount is at most 5% by weight, such as at least at most 4% by weight or at most 3% by weight or at most 2% by weight, more preferably at most 1% by weight.

Therefore, the present invention also relates to the above discussed oral solid dosage form, comprising at most 5% by weight, preferably at most 1% by weight, in each case relative to the sorafenib tosylate form III, of sorafenib tosylate form I.

Usually, the content of the oral solid dosage form of the present invention with regard to the sorafenib tosylate form III, relative to the total weight of the oral solid dosage form, is at least 10% by weight or at least 20% by weight or at least 30% by weight. Preferably, said content is at least 40% by weight, preferably at least 50% by weight, more preferably at least 60% by weight, more preferably at least 70% by weight, more preferably at least 75% by weight, more preferably in the range of from 75 to 95% by weight, more preferably of from 80 to 90% by weight. Therefore, the present invention relates to the oral solid dosage form, comprising the sorafenib tosylate form III in an amount of at least 40% by weight, preferably of at least 75% by weight, more preferably of from 80 to 90% by weight, in each case relative to the total weight of the oral dosage form.

The oral solid dosage form of the present invention comprises at least one excipient. Generally, there are no specific restrictions concerning the chemical nature of these excipients provided that the excipient or mixture of excipients comprised in the oral solid dosage form is/are pharmaceutically acceptable. A pharmaceutically acceptable excipient is any excipient which is relatively non-toxic and innocuous to a patient at concentrations consistent with effective activity of the crystalline sorafenib tosylate so that any side effects ascribable to the excipient do not vitiate the beneficial effects of the crystalline sorafenib tosylate. Therefore, according to the present invention, excipients are, for example, disintegrants, binders, lubricants, fillers, plasticizers, surfactants and wetting agents, film-forming agents and coating materials, sweeteners, flavoring agents, and coloring agents such as example pigments. Other excipients known in the field of pharmaceutical compositions may also be used.

Suitable disintegrants according to the present invention include, but are not limited to, carboxymethylcellulose calcium, carboxymethylcellulose sodium, croscarmellose (crosslinked carboxymethylcellulose) sodium, cross-linked polyvinylpyrrolidone, crospovidone (cross-linked povidone, a synthetic cross-linked homopolymer of N-vinyl-2-pyrrolidone), alginic acid, microcrystalline cellulose (such as refined wood pulp derived from alpha cellulose), hydroxypropyl cellulose, low substituted hydroxypropyl cellulose, polacrillin potassium, sodium alginate, sodium starch glycolate, partially hydrolysed starch, sodium carboxymethyl starch, and starch.

Suitable binders according to the present invention include, but are not limited to, hydroxypropyl cellulose, hypromellose (hydroxypropyl methylcellulose, HPMC), microcrystalline cellulose, acacia, alginic acid, carboxymethylcellulose, ethylcellulose, methylcellulose, hydroxyethylcellulose, ethylhydroxyethylcellulose, polyvinyl alcohol, polyacrylates, carboxymethylcellulose calcium, carboxymethyl cellulose sodium, compressible sugar, ethylcellulose, gelatin, liquid glucose, methylcellulose, polyvinyl pyrrolidone and pregelatinized starch.

Suitable lubricants according to the present invention include, but are not limited to, calcium stearate, magnesium stearate, mineral oil, stearic acid, fumaric acid, sodium stearylfumarate, zinc stearate and polyethylene glycol.

Suitable fillers according to the present invention include, but are not limited to, dibasic calcium phosphate, kaolin, microcrystalline cellulose, silicated microcrystalline cellulose, dicalcium phosphate, tricalcium phosphate, magnesium trisilicate, lactose such as example the anhydrous form or the hydrate form such as the monohydrate form, sugars such as dextrose, maltose, saccharose, glucose, fructose or maltodextrine, sugar alcohols such as mannitol, maltitol, sorbitol, xylitol, powdered cellulose, precipitated calcium carbonate, sodium carbonate, sodium phosphate and starch.

Suitable surfactants and wetting agents according to the present invention include, but are not limited to, heptadecaethylene oxycetanol, lecithins, sorbitol monooleate, polyoxyethylene sorbitol monooleate, polyoxyethylene stearate, polyoxyethylen sorbitan monolaurate, benzalkonium chloride, nonoxynol 10, oxtoxynol 9, polysorbates, for example polysorbate 20, polysorbate 40, polysorbate 60 or polysorbate 80, sorbitan monopalmitate, sodium salts of fatty alcoholsulfates such as sodium lauryl sulfate, sodium dodecylsulfate, sodium salts of sulfosuccinates such as sodium dioctylsulfosuccinate, partially esters of fatty acids with alcohols such as glycerine monostearate, partially esters of fatty acids with sorbitans such as sorbitan monolaurate, partially esters of fatty acids with polyhydroxyethylene sorbitans such as polyethyleneglycol sorbitan monolaurate, -monostearate or -monooleate, ethers of fatty alcohols with polyhydroxyethylene, esters of fatty acids with polyhydroxyethylene, copolymers of ethylenoxide and propylenoxide (Pluronic®) and ethoxylated triglycerides.

Suitable film-forming agents and coating materials according to the present invention include, but are not limited to, liquid glucose, hydroxyethyl cellulose, hydroxypropyl cellulose, hydroxypropyl methylcellulose (hypromellose, HPMC), methylcellulose, ethylcellulose, cellulose acetate phthalate, shellac, polyvinylpyrrolidone, copolymers of vinylpyrrolidone and vinylacetate such as Kollidon® VA64 BASF, copolymers of acrylic and/or methacrylic acid esters with trimethylammoniummethylacrylate, copolymers of dimethylaminomethacrylic acid and neutral methacrylic acid esters, polymers of methacrylic acid or methacrylic acid esters, copolymers of acrylic acid ethylester and methacrylic acid methyl ester, and copolymers of acrylic acid and acrylic acid methylester.

Suitable plasticizers according to the present invention include, but are not limited to, polyethylene glycol, diethyl phthalate and glycerol. Preference is given to polyethylene glycol.

Suitable coloring agents according to the present invention include, but are not limited to, pigments, inorganic pigments, FD&C Red No. 3, FD&C Red No. 20, FD&C Yellow No. 6, FD&C Blue No. 2, D&C Green No. 5, D&C Orange No. 5, D&C Red No. 8, caramel, ferric oxide red, ferric oxide yellow and titanium dioxide.

Suitable further commonly used excipients which may be used according to the present invention include, but are not limited to, acidifying agents such as acetic acid, citric acid, fumaric acid, hydrochloric acid and nitric acid; alkalizing agents such as ammonia solution, ammonium carbonate, diethanolamine, monoethanolamine, potassium hydroxide, sodium borate, sodium carbonate, sodium hydroxide, triethanolamine and trolamine; adsorbents such as powdered cellulose and activated charcoal; stabilizers and antioxidants such as ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate and sodium metabisulfite; binding materials such as block polymers, natural and synthetic rubber, polyacrylates, polyurethanes, silicones, polysiloxanes and styrene-butadiene copolymers; buffering agents such as potassium metaphosphate, dipotassium phosphate, sodium acetate, sodium citrate anhydrous and sodium citrate hydrates; encapsulating agents such as gelatin, starch and cellulose derivates; flavorants, masking agents and odors such as anise oil, cinnamon oil, cocoa, menthol, orange oil, peppermint oil and vanillin; humectants such as glycerol, propylene glycol and sorbitol; sweeteners such as aspartame, dextrose, glycerol, mannitol, propylene glycol, saccharin sodium, sorbitol and sucrose; anti-adherents such as magnesium stearate and talc; direct compression excipients such as dibasic calcium phosphate, lactose and microcrystalline cellulose; tablet polishing agents such as carnauba wax and white wax.

The oral solid dosage form of the present invention is a compressed or a non-compressed dosage form. Preferably, the oral solid dosage form of the present invention is a granule, a capsule, for example a capsule filled with granules, a sachet, a pellet, a dragee, a lozenge, a troche, a pastille, or a tablet, such as an uncoated tablet, a coated tablet, an effervescent tablet, a soluble tablet, a dispersible tablet, an orodispersible tablet, a tablet for use in the mouth, a chewable tablet or an extrudate. Preferably, the longest dimension of an oval tablet or of a capsule is at most 25 mm; as to a round tablet should, a preferred diameter is at most 13 mm.

Immediate Release Tablet

According to a preferred embodiment of the present invention, the oral solid dosage form is a compressed dosage form. More preferably, the oral solid dosage form is a tablet, and even more preferably, it is an immediate release tablet. Compressed dosage forms can be prepared by compressing uniform volumes of particles or particle aggregates, preferably produced by granulation methods. In the manufacture of such tablets, means are taken to ensure that they possess a suitable mechanical strength to avoid crumbling or breaking on handling or subsequent processing. The process of providing compressed dosage forms is well known to the skilled person.

According to this embodiment, the oral solid dosage form of the present invention preferably comprises at least one excipient selected from the group consisting of fillers, disintegrants, binders, lubricants, and surfactants. More preferably, the oral solid dosage form of the present invention comprises at least one filler and at least one disintegrant and at least one binder and at least one lubricant and at least one surfactant. Even more preferably, the oral solid dosage form comprises at least one filler, preferably microcrystalline cellulose, in an amount of from 2 to 55, preferably from 2 to 6% by weight, at least one disintegrant, preferably croscarmellose, in an amount of from 4 to 12, preferably from 6 to 12% by weight, at least one binder, preferably hypromellose, in an amount of from 0.25 to 8, preferably from 0.5 to 5% by weight, at least one lubricant, preferably magnesium stearate, in an amount of from 0.1 to 1.0, preferably from 0.2 to 0.8% by weight, and at least one surfactant, preferably sodium lauryl sulfate, in an amount of from 0.1 to 1.0, preferably from 0.2 to 0.8% by weight, in each case relative to the total weight of the oral dosage form.

According to this embodiment, the oral solid dosage form most preferably comprises the sorafenib tosylate form III in an amount of at least 75% by weight, more preferably from 75 to 95% by weight, more preferably of from 80 to 90% by weight, in each case relative to the total weight of the oral dosage form.

Usually, the dissolution rate of the oral solid dosage form according to this embodiment of the present invention is at least 50%. Preferably, the dissolution rate is at least 60%, more preferably at least 70%, and in particular at least 80%.

According to an especially preferred embodiment, the present invention relates to an immediate release tablet comprising sorafenib tosylate form III in an amount of from 80 to 90% by weight, microcrystalline cellulose in an amount of from 2 to 6% by weight, croscarmellose in an amount of from 6 to 12% by weight, hypromellose in an amount of from 0.5 to 5% by weight, magnesium stearate in an amount of from 0.2 to 0.8% by weight, sodium lauryl sulfate in an amount of from 0.2 to 0.8% by weight, in each case relative to the total weight of the oral dosage form, and sorafenib tosylate form I in an amount of at most 1% by weight relative to the sorafenib tosylate form III.

As to this especially preferred embodiment of the present invention, it was found that the dissolution rate is above 80%.

Dispersible Tablet

According to another embodiment of the present invention, the oral solid dosage form is a dosage form in the form a dispersible tablet or granule. More preferably, the oral solid dosage form is a dispersible tablet.

Surprisingly, it was found that advantageous granules and tablets, in particular tablets, can be prepared if at least one excipient is used in combination with the sorafenib tosylate form III, which excipient is selected from the group consisting of sugars, sugar alcohols, oligosaccharides, pharmaceutically acceptable polyvinyl derivatives, pharmaceutically acceptable polyalkylene glycols, and a mixture of two or more thereof.

According to this embodiment, the oral solid dosage form of the present invention preferably comprises at least one first filler selected from the group consisting of sugars such as dextrose, maltose, saccharose, glucose, fructose, trehalose; sugar alcohols such as mannitol, maltitol, sorbitol, xylitol; oligosaccharides, such as maltodextrine; pharmaceutically acceptable polyvinyl derivatives such as povidone (polyvinyl pyrrolidone) or polyvinyl alcohol; pharmaceutically acceptable polyalkylene glycols such as polyethylene glycol; and mixtures of two or more thereof; and optionally at least one second filler, at least one disintegrant and at least one surfactant. Even more preferably, the oral solid dosage form comprises at least one first filler selected from the group consisting of sugars, sugar alcohols, oligosaccharides, pharmaceutically acceptable polyvinyl derivatives, pharmaceutically acceptable polyalkylene glycols, and mixtures of two or more thereof, preferably saccharose and/or mannitol and/or povidone, more preferably mannitol, in an amount of from 5 to 55% by weight, at least one second filler, preferably microcrystalline cellulose, in an amount of from 1 to 10% by weight, at least one disintegrant, preferably sodium starch glycolate, in an amount of from 1 to 10% by weight, and optionally of from 1 to 5% by weight of a surfactant, in each case relative to the total weight of the oral dosage form.

The presently marketed dosage form comprising crystalline sorafenib form I requires the presence of a specific surfactant, namely sodium lauryl sulfate which is probably used in order to allow for a sufficient dispersibility of the dosage form. However, such a strong surfactant such as sodium lauryl sulfate may impair both the taste and the tolerability of the oral dosage form. In particular, this might become a problem if the oral dosage form has to be dispersed and disintegrated in water in case, for example, the patient in need of the oral dosage form has swallowing problems.

Surprisingly, it was found that using the crystalline sorafenib tosylate having polymorphic form III as active agent comprised in an oral solid dosage form allows for substituting such strong surfactants like sodium lauryl sulfate by a phospholipid, preferably by a lecithin which has a better taste. In contrast to sodium lauryl sulfate, lecithin is an endogenous substance and also present in many foods. It can even be administered intravenously up to concentrations as present in the oral dosage form of this invention. This can be regarded as a strong indicator for a very good tolerability.

Therefore, the present invention relates to said oral solid dosage form, comprising at least one first filler selected from the group consisting of sugars, sugar alcohols, oligosaccharides, pharmaceutically acceptable polyvinyl derivatives, pharmaceutically acceptable polyalkylene glycols, and mixtures of two or more thereof, preferably saccharose and/or mannitol and/or povidone, in an amount of from 5 to 55% by weight, at least one at least one second filler, preferably microcrystalline cellulose, in an amount of from 1 to 10% by weight, at least one disintegrant, preferably sodium starch glycolate, in an amount of from 1 to 10% by weight, and optionally of from 1 to 5% by weight of a surfactant, preferably a phospholipid, more preferably a lecithin, wherein said dosage form comprises less than 0.1% by weight, preferably less than 0.001% by weight, of sodium lauryl sulfate, preferably of a lauryl sulfate.

Even more surprisingly, it was found that using the sorafenib tosylate form III as active agent comprised in an oral solid dosage form allows for either minimizing the amount of surfactant or even completely avoiding the presence of a surfactant in the oral dosage form.

Therefore, the present invention relates to said oral solid dosage form, comprising at least one first filler selected from the group consisting of sugars, sugar alcohols, oligosaccharides, pharmaceutically acceptable polyvinyl derivatives, pharmaceutically acceptable polyalkylene glycols, and mixtures of two or more thereof, preferably saccharose and/or mannitol and/or povidone, in an amount of from 5 to 55% by weight, at least one at least one second filler, preferably microcrystalline cellulose, in an amount of from 1 to 10% by weight, at least one disintegrant, preferably sodium starch glycolate, in an amount of from 1 to 10% by weight, wherein said dosage form comprises less than 0.1% by weight, preferably less than 0.001% by weight.

Method for the Preparation of the Oral Solid Dosage Form

Generally, there are no specific restrictions concerning the method for the preparation of the oral solid dosage form according to the present invention provided that oral dosage form are obtained.

Preferably, the present invention relates to a method for the preparation of an oral solid dosage form, preferably of the oral solid dosage form as discussed above, said method comprising a) providing sorafenib tosylate form III;
b) mixing the sorafenib tosylate form III provided in a) with at least one excipient;
c) preparing the oral solid dosage form based on the mixture obtained in b).

Concerning possible excipients, reference is made to the excipients described above. Most preferably, the sorafenib tosylate form III and the at least one excipient are employed in amounts which allow for obtaining the oral solid dosage form as described above.

Preferably, the oral solid dosage forms are prepared by granulation according to which method the sorafenib tosylate form III provided in a) and at least one excipient are granulated to obtain a granulate, optionally followed by blending the obtained granulate with at least one further excipient. The granulate, or optionally the blended granulate, can be optionally coated with at least one further excipient.

The granulation of the sorafenib tosylate form III provided in a) and the at least one excipient is preferably carried out as a wet-granulation process. According to such wet-granulation process, the sorafenib tosylate form III provided in a) and the at least one excipient are preferably admixed with a suitable granulation liquid, preferably water, and granulated. Prior to mixing, the water can be admixed with at least one excipient; in this case, it is preferred to admix at least one of the surfactants with the water, if such a surfactant is employed at all.

The granulation can be performed according to all conceivable methods. For example, in case the oral dosage form is to be prepared in large-scale numbers, a high-shear mixer can be employed. The damp mass obtained can then be passed through a sieve such as an oscillating sieve with, for example, a 1-4 mm mesh size. In case the oral dosage form is to be prepared in small-scale numbers, mixing can be performed manually such as with a mortar and a pistil, and the granulation can be performed by making use of a suitably-sized sieve such as a prescription sieve with, for example, a 1-4 mm mesh size. The granulates obtained are preferably suitably dried, such as in a fluidized-bed dryer tray dryer, at preferred temperatures in the range of from 50 to 120° C., preferably from 80 to 100° C. until the residual moisture content of the oral solid dosage form is preferably at most 3% by weight, more preferably at most 2% by weight, more preferably at most 1% by weight. Optionally after drying, the dried granules can be sieved again.

After the granulation process, the preferably dried granulates can be optionally blended with at least one further excipient, preferably a lubricant, more preferably magnesium stearate and/or preferably with a disintegrant, more preferably croscarmellose sodium. Any conceivable device can be employed for such blending process. A suitable device is, for example, a tumbler blender, and typical tumbling times are with a range of from 5 to 10 minutes.

The preferably dried granulates, optionally blended with at least one excipient, are then optionally compacted to give the optionally blended granulate a desired shape, such as the shape of a pastille, a pellet, or preferably a tablet.

Therefore, the present invention relates to the method above, wherein in c), the oral solid dosage form based on the mixture obtained in b) is prepared by
c1) granulating, preferably wet-granulating the mixture obtained in b), wherein as granulation liquid, water is employed optionally comprising at least one excipient;
c2) optionally blending the granulate obtained in c1) with at least one excipient;
c3) optionally compressing the optionally blended granulate.

Subsequently, the optionally blended and/or optionally compacted, preferably compressed granulate can be suitably coated such as film-coated with at least one excipient. This at least one excipient is preferably selected from the group consisting of film-forming agents, plasticizers and coloring agents. Suitable film-forming agents, plasticizers and coloring agents are described above. Therefore, the present invention also relates to a process as described above, additionally comprising
d) coating the compacted, preferably compressed granulate with at least one excipient.

The oral solid dosage form of the present invention comprising the sorafenib tosylate form III is preferably used in the treatment of mammalian hyper-proliferate disorders, including cancer, said disorder optionally being renal cell carcinoma or hepatocellular carcinoma.

As discussed above, the oral solid dosage form of the present invention, compared to the known dosage form comprising the sorafenib tosylate form I, is characterized by a lower susceptibility to humidity. It has thus better properties when stored in a humid environment for a prolonged period of time in comparison to solid dosage forms containing form I. Therefore, the oral solid dosage form of the present invention is particularly useful if it is to be employed in a country having a tropical climate. In this case, in contrast to the currently marketed tablets of Nexavar®, it is not necessary to package the inventive oral solid dosage form in aluminum blisters. Therefore, this advantageous characteristic of the oral dosage form according to the present invention allows for a cheaper packaging material. Preferred packaging materials have a vapour transmission rate of at least $0.4 \text{ g m}^{-2} \text{ d}^{-1}$, preferably of at least $1 \text{ g m}^{-2} \text{ d}^{-1}$, more preferably of at least $2 \text{ g m}^{-2} \text{ d}^{-1}$, as measured according to standard DIN 53122-1. Some preferred packaging materials are polyethylene, polyethylene terephthalate, polystyrene, and polyvinyl chloride. Other preferred packaging materials are polypropylene and polyvinylidene chloride.

Therefore, the present invention also relates to the oral solid dosage form as described above for use in the treatment of mammalian hyper-proliferate disorders, including cancer, said disorder optionally being renal cell carcinoma or hepatocellular carcinoma, wherein the oral dosage form is to be administered to patients in a country having an area with an Af or an Am climate, preferably an Af climate, according to the Köppen-Geiger climate classification.

Generally, the present invention also relates to sorafenib tosylate form III for use in the treatment of mammalian hyper-proliferate disorders, including cancer, said disorder optionally being renal cell carcinoma or hepatocellular carcinoma, wherein the oral dosage form is to be administered to patients in a country having an area with an Af or an Am climate, preferably an Af climate, according to the Köppen-Geiger climate classification.

Further, as described above, the use of the sorafenib tosylate form III as pharmaceutically active agent in oral solid dosage form, if used as substitute for the sorafenib tosylate form I, allows for the preparation of oral solid dosage forms which have an increased dissolution rate after storage. This increased dissolution rate is an indication of the increased storage stability of an oral solid dosage form.

Consequently, the present invention generally relates to the use of sorafenib tosylate form III for the improvement of the storage stability of an oral solid dosage form comprising crystalline sorafenib tosylate.

Further, the present invention relates to the use of sorafenib tosylate form III for the preparation of an oral solid dosage form having an increased dissolution rate after packaging in a polyethylene film and storage in the dark at 40° C. at a relative humidity of 75% for a period of at least 14 days, compared to an identically packaged and stored oral solid dosage form comprising, instead of sorafenib tosylate form III, the sorafenib tosylate form I.

Pharmaceutical Composition

The above-described advantage of the sorafenib tosylate form III with regard to an improved, i.e. lower susceptibility to humidity compared to the sorafenib tosylate form I is not restricted to above-described oral solid dosage form.

Therefore, the present invention generally also relates to a pharmaceutical composition comprising crystalline sorafenib tosylate form III, wherein said pharmaceutical composition is packaged in a packaging material having a moisture vapour transmission rate of at least $0.4 \text{ g m}^{-2} \text{ d}^{-1}$ as measured according to standard DIN 53122-1, said packaging material preferably being made from polyethylene, polypropylene, polyvinylidene chloride and/or polyvinylchloride.

While the present invention has been described with respect to some preferred embodiments, this is in no way to limit the scope of the invention. The person skilled in the art is clearly aware of further embodiments and variations to the above-described embodiments which are still within the scope of the present invention.

EXAMPLES

Reference Example 1

Analytical Methods a) Tablet Storage

The tablets were packaged and stored in the dark at 40° C. at a relative humidity of 75% for a period of 14 days.

b) Dissolution Test

Dissolution testing of the tablets stored according to a) was performed using an USP 2 apparatus with a stirrer speed of 75 rpm and a test temperature of 37° C. Dissolution medium was 900 ml of a 0.1 N HCl solution with 1% sodium dodecyl sulphate.

Sampling was performed automatically and the drug concentration was measured by UV detection at 263 nm.

Alternatively, the samples were analyzed by HPLC using the following parameters:

HPLC system with gradient pump, thermostated sampler, thermostated column oven and diode array detector (Agilent 1200 system)

HPLC conditions

Column: length 150 mm, internal diameter 4.6 mm (at 30° C.)

USP L11 stationary phase (5 micrometer)

Mobile Phase: A: water+0.2% acetic acid, B: acetonitrile

Run type: gradient elution from 15% mobile Phase B to 95% mobile Phase B in 25 minutes Detection: 254 nm (and spectra from 190-400 nm)

c) Disintegration Test

Disintegration was tested visually by placing a tablet in a glass of water (about 150 ml) at room temperature.

d) X-Ray Powder Diffraction

X-ray powder diffraction patterns (XRPD) were obtained with a PANalytical X'Pert PRO diffractometer equipped with a theta/theta coupled goniometer in transmission geometry, Cu-Kalpha1,2 radiation (wavelength 0.15419 nm) with a focusing mirror and a solid state PIXcel detector. The patterns were recorded at a tube voltage of 45 kV and a tube current of 40 mA, applying a stepsize of 0.013° 2-theta with 40 s per step (255 channels) in the angular range of 2° to 40° 2-theta at ambient conditions.

e) Raman Spectroscopy

The Raman results were generated with a Renishaw inVia Raman Microscope and the following instrument settings:

Magnification: 20×

Laser: 532 nm

Laser power: 100%

Exposure time: 2 seconds

Spectra range: 272-2015 $cm^{-1}$

Reference Example 2

Identification of Sorafenib Tosylate Form III and I a) Identification of Polymorph III Crystalline sorafenib tosylate of polymorphic form III was analyzed via X-ray diffraction as described in Reference Example 1 d). An X-ray powder diffraction pattern was obtained which is shown in FIG. 1 and which is also characterized by the following Table 1. In particular, it is noted that no traces of sorafenib tosylate of polymorphic form I were detected.

TABLE 1

X-ray powder diffraction pattern polymorph form III

| No. | Pos. [2 theta.] | d-spacing [Angstrom] | Height [cts] | Rel. Int. [%] |
|---|---|---|---|---|
| 1 | 7.6862 | 11.50233 | 80.91 | 8.49 |
| 2 | 8.5764 | 10.31028 | 70.94 | 7.44 |
| 3 | 9.848 | 8.98167 | 29.78 | 3.12 |
| 4 | 10.6339 | 8.31959 | 134.82 | 14.14 |
| 5 | 12.0145 | 7.36654 | 518.39 | 54.37 |
| 6 | 12.3594 | 7.16173 | 60.71 | 6.37 |
| 7 | 12.9793 | 6.82101 | 114.4 | 12 |
| 8 | 13.3722 | 6.62146 | 64.71 | 6.79 |
| 9 | 13.5468 | 6.53651 | 55.8 | 5.85 |
| 10 | 16.0829 | 5.51106 | 272.4 | 28.57 |
| 11 | 16.5205 | 5.36604 | 28.52 | 2.99 |
| 12 | 16.8813 | 5.25215 | 52.53 | 5.51 |
| 13 | 17.3738 | 5.10437 | 191.84 | 20.12 |
| 14 | 17.7873 | 4.98662 | 404.64 | 42.44 |
| 15 | 18.7383 | 4.73564 | 168.18 | 17.64 |
| 16 | 19.3705 | 4.58249 | 401.45 | 42.1 |
| 17 | 19.9191 | 4.4575 | 953.5 | 100 |
| 18 | 20.3135 | 4.37184 | 273.09 | 28.64 |
| 19 | 20.8874 | 4.253 | 269.59 | 28.27 |
| 20 | 21.235 | 4.18415 | 53.5 | 5.61 |
| 21 | 21.6379 | 4.10714 | 552.2 | 57.91 |
| 22 | 22.5485 | 3.9433 | 192.64 | 20.2 |
| 23 | 23.0389 | 3.86046 | 93.15 | 9.77 |
| 24 | 23.4027 | 3.80127 | 67.57 | 7.09 |
| 25 | 24.2366 | 3.67233 | 293.68 | 30.8 |
| 26 | 24.5442 | 3.62701 | 38.24 | 4.01 |
| 27 | 24.9093 | 3.57467 | 54.2 | 5.68 |
| 28 | 25.2897 | 3.52175 | 29.34 | 3.08 |
| 29 | 25.9612 | 3.43216 | 304.19 | 31.9 |
| 30 | 26.9354 | 3.3102 | 96.52 | 10.12 |
| 31 | 27.5273 | 3.24036 | 121.71 | 12.76 |
| 32 | 27.7475 | 3.21514 | 153.61 | 16.11 |
| 33 | 28.2122 | 3.16323 | 59.63 | 6.25 |
| 34 | 29.278 | 3.05046 | 79.74 | 8.36 |
| 35 | 29.4515 | 3.03288 | 78.13 | 8.19 |
| 36 | 29.8767 | 2.99068 | 149.23 | 15.65 |
| 37 | 31.51 | 2.83590 | 117.24 | 12.3 |
| 38 | 32.2769 | 2.77356 | 68.99 | 7.24 |
| 39 | 33.6129 | 2.66631 | 27.66 | 2.9 |
| 40 | 34.1075 | 2.62878 | 26.78 | 2.81 |
| 41 | 35.3003 | 2.54263 | 34.45 | 3.61 |
| 42 | 36.182 | 2.48267 | 20.65 | 2.17 |

TABLE 1-continued

X-ray powder diffraction pattern polymorph form III

| No. | Pos. [2 theta.] | d-spacing [Angstrom] | Height [cts] | Rel. Int. [%] |
|---|---|---|---|---|
| 43 | 37.2552 | 2.41359 | 21.78 | 2.28 |
| 44 | 37.8016 | 2.37995 | 16.46 | 1.73 |

Figure 2:
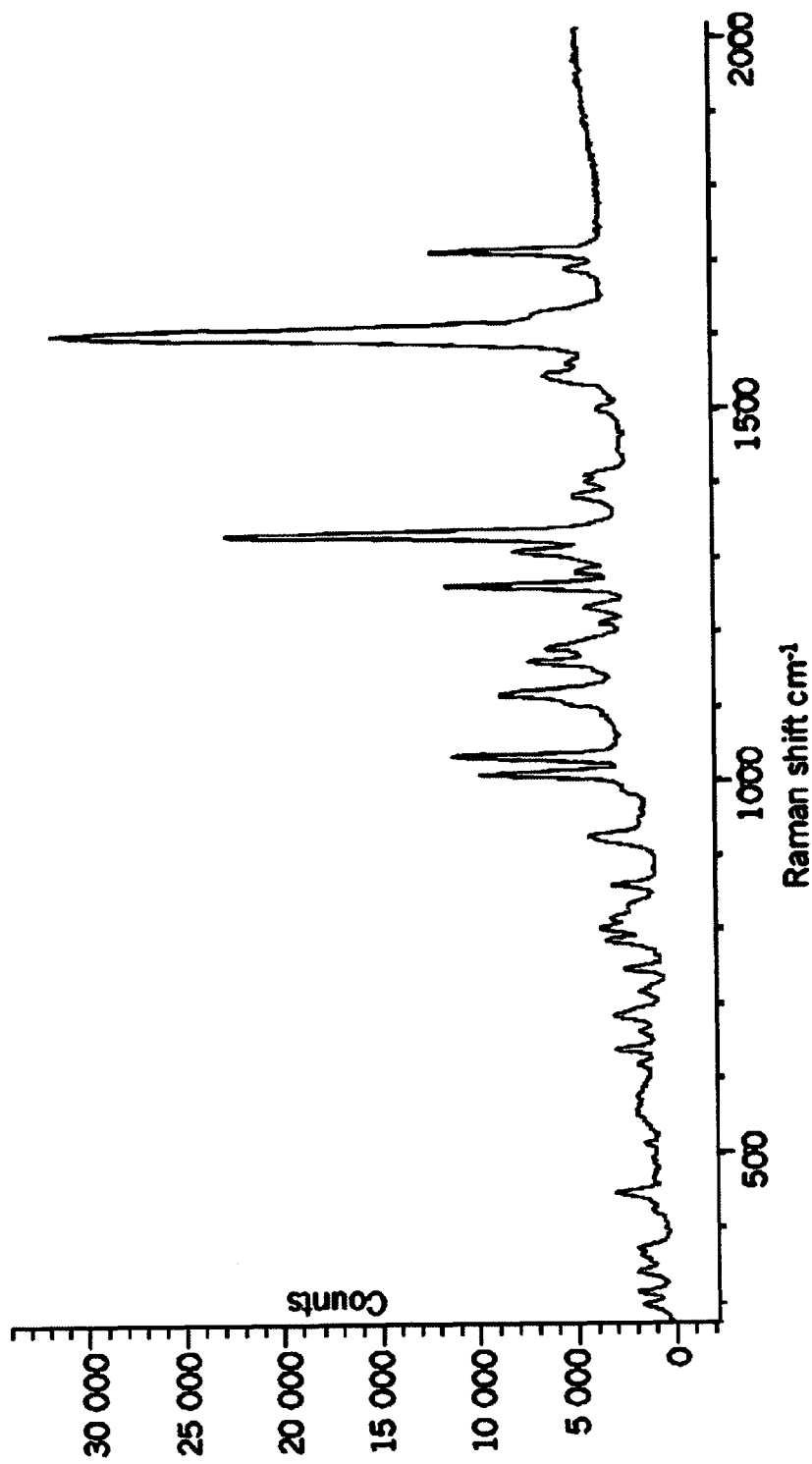
FIG. 2: Raman spectrum of sorafenib tosylate polymorphic form III analyzed according to Reference Example 1 e). On the x axis, the Raman shift/cm−1 is shown with explicit values of 500, 1000, 1500, and 2000. On the y axis, the counts are shown with explicit values of from 5000 to 35000.

Further, the obtained crystalline compound was characterized by Raman spectroscopy as described in Reference Example 1 e). The following peak table (Table 2) was obtained. Again, no traces of sorafenib tosylate of polymorphic form I were detected. The Raman spectrum is shown in FIG. 2.

TABLE 2

Raman spectrum peak table polymorph form III

| Raman shift [cm$^{-1}$] | Intensity | Relative Intensity |
|---|---|---|
| 1715 | 9000 | 31.0 |
| 1688 | 1500 | 5.2 |
| 1630 | 4300 | 14.8 |
| 1601 | 29000 | 100.0 |
| 1545 | 3500 | 12.1 |
| 1501 | 1000 | 3.4 |
| 1412 | 1000 | 3.4 |
| 1404 | 1000 | 3.4 |
| 1386 | 1500 | 5.2 |
| 1334 | 21000 | 72.4 |
| 1310 | 6000 | 20.7 |
| 1268 | 10000 | 34.5 |
| 1234 | 2000 | 6.9 |
| 1213 | 1500 | 5.2 |
| 1180 | 4500 | 15.5 |
| 1163 | 7500 | 25.9 |
| 1117 | 7000 | 24.1 |
| 1033 | 9500 | 32.8 |
| 1011 | 9000 | 31.0 |
| 924 | 3500 | 12.1 |
| 863 | 2400 | 8.3 |
| 825 | 1700 | 5.9 |
| 816 | 2600 | 9.0 |
| 803 | 3200 | 11.0 |
| 786 | 3000 | 10.3 |
| 745 | 1800 | 6.2 |
| 685 | 2200 | 7.6 |
| 639 | 2500 | 8.6 |
| 621 | 1200 | 4.1 |
| 513 | 1000 | 3.4 |
| 450 | 2500 | 8.6 |
| 427 | 1500 | 5.2 | b) Identification of Polymorph I

Figure 3:
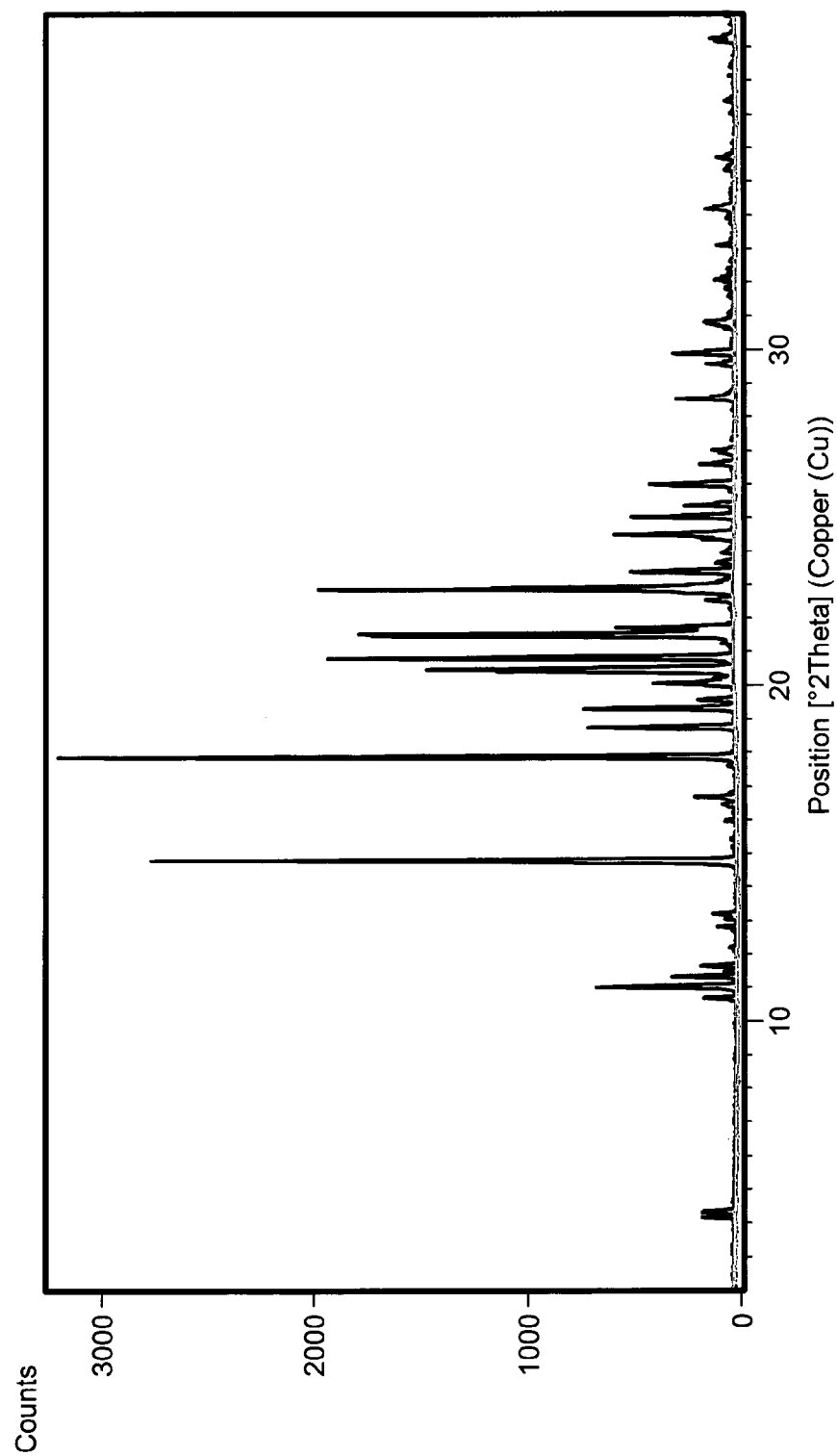
FIG. 3: XRPD pattern of sorafenib tosylate polymorphic form I analyzed according to Reference Example 1 d). On the x axis, the position [° 2 Theta] (Copper (Cu)) is shown with explicit values of 10, 20, and 30 being explicitly shown. On the y axis, the counts are shown with explicit values of 0, 1000, 2000, and 3000.

Crystalline sorafenib tosylate of polymorphic form I was analyzed via X-ray diffraction as described in Reference Example 1 d). An X-ray powder diffraction pattern was obtained which is shown in FIG. 3 and which is also characterized by the following Table 3.

TABLE 3

X-ray powder diffraction pattern polymorph form I

| No. | Pos. [2 theta.] | d-spacing [Angstrom] | Height [cts] | Rel. Int. [%] |
|---|---|---|---|---|
| 1 | 4.1684 | 21.19806 | 166.03 | 5.12 |
| 2 | 4.317 | 20.46879 | 150.12 | 4.63 |
| 3 | 10.68 | 8.28382 | 161.05 | 4.96 |
| 4 | 11.0189 | 8.02309 | 661.42 | 20.38 |
| 5 | 11.3304 | 7.80323 | 312.87 | 9.64 |

TABLE 3-continued

X-ray powder diffraction pattern polymorph form I

| No. | Pos. [2 theta.] | d-spacing [Angstrom] | Height [cts] | Rel. Int. [%] |
|---|---|---|---|---|
| 6 | 11.4904 | 7.69495 | 56.68 | 1.75 |
| 7 | 11.6377 | 7.59788 | 178.76 | 5.51 |
| 8 | 12.1922 | 7.25351 | 37.71 | 1.16 |
| 9 | 12.8007 | 6.91008 | 102.73 | 3.17 |
| 10 | 13.0532 | 6.77694 | 67.88 | 2.09 |
| 11 | 13.1975 | 6.70317 | 122.43 | 3.77 |
| 12 | 14.7773 | 5.98993 | 2844.9 | 87.65 |
| 13 | 15.1813 | 5.83141 | 28.62 | 0.88 |
| 14 | 15.4173 | 5.74268 | 24.31 | 0.75 |
| 15 | 15.9732 | 5.54407 | 51.67 | 1.59 |
| 16 | 16.4379 | 5.38834 | 72.41 | 2.23 |
| 17 | 16.6681 | 5.31444 | 207.74 | 6.4 |
| 18 | 17.6053 | 5.03359 | 42.34 | 1.3 |
| 19 | 17.8505 | 4.965 | 3245.86 | 100 |
| 20 | 18.7467 | 4.72963 | 695.69 | 21.43 |
| 21 | 19.2996 | 4.59535 | 653.07 | 20.12 |
| 22 | 19.5723 | 4.53193 | 178.65 | 5.5 |
| 23 | 20.0483 | 4.4254 | 392.54 | 12.09 |
| 24 | 20.4708 | 4.335 | 1484.24 | 45.73 |
| 25 | 20.8063 | 4.26586 | 1922.9 | 59.24 |
| 26 | 21.4623 | 4.13692 | 1689.57 | 52.05 |
| 27 | 21.5202 | 4.12592 | 1784.52 | 54.98 |
| 28 | 21.7102 | 4.09024 | 546.35 | 16.83 |
| 29 | 22.5285 | 3.94349 | 135.6 | 4.18 |
| 30 | 22.855 | 3.88789 | 2016.5 | 62.13 |
| 31 | 23.3816 | 3.8015 | 494.07 | 15.22 |
| 32 | 23.6385 | 3.76077 | 86.19 | 2.66 |
| 33 | 23.9384 | 3.71432 | 59.8 | 1.84 |
| 34 | 24.3442 | 3.65333 | 160.57 | 4.95 |
| 35 | 24.4742 | 3.63422 | 576.12 | 17.75 |
| 36 | 25.0223 | 3.55583 | 499.79 | 15.4 |
| 37 | 25.3611 | 3.5091 | 238.61 | 7.35 |
| 38 | 25.9821 | 3.42661 | 375.13 | 11.56 |
| 39 | 26.581 | 3.35076 | 177.61 | 5.47 |
| 40 | 27.0063 | 3.29894 | 112.78 | 3.47 |
| 41 | 27.3269 | 3.26096 | 16.77 | 0.52 |
| 42 | 28.5293 | 3.1262 | 285.9 | 8.81 |
| 43 | 29.5599 | 3.01951 | 122.73 | 3.78 |
| 44 | 29.8796 | 2.98793 | 299.02 | 9.21 |
| 45 | 30.8483 | 2.89627 | 149.69 | 4.61 |
| 46 | 31.601 | 2.82898 | 25.23 | 0.78 |
| 47 | 31.8098 | 2.81089 | 47.02 | 1.45 |
| 48 | 32.0675 | 2.78888 | 101.05 | 3.11 |
| 49 | 32.3969 | 2.76127 | 29.69 | 0.91 |
| 50 | 32.6411 | 2.74117 | 25.33 | 0.78 |
| 51 | 33.0929 | 2.70477 | 92.44 | 2.85 |
| 52 | 34.1792 | 2.62125 | 142.26 | 4.38 |
| 53 | 35.3667 | 2.53591 | 37.31 | 1.15 |
| 54 | 35.6924 | 2.51352 | 82.87 | 2.55 |
| 55 | 37.0513 | 2.42439 | 23.42 | 0.72 |
| 56 | 37.3938 | 2.40296 | 39.85 | 1.23 |
| 57 | 38.1168 | 2.35903 | 28.61 | 0.88 |
| 58 | 38.4278 | 2.34065 | 23.58 | 0.73 |
| 59 | 39.2534 | 2.2933 | 124.25 | 3.83 |

Figure 4:
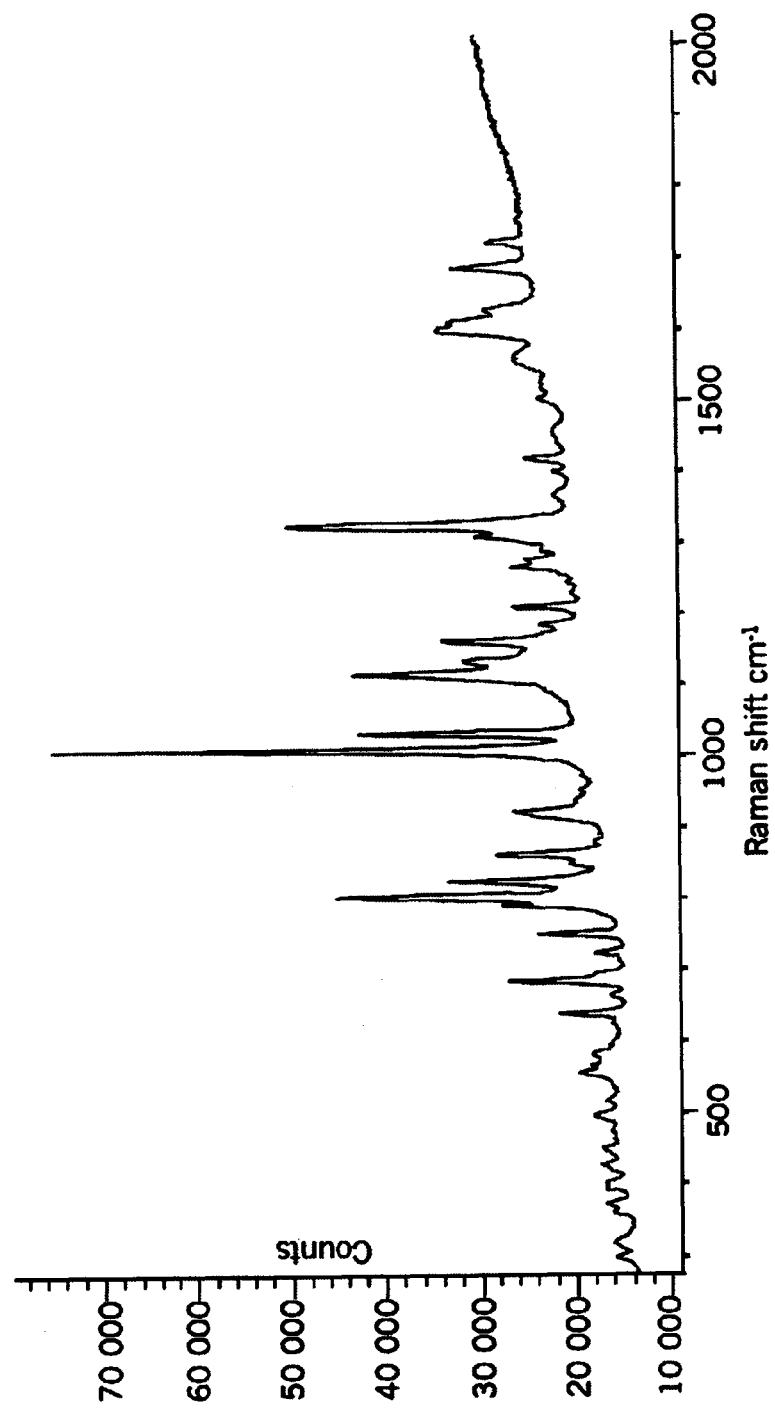
FIG. 4: Raman spectrum of sorafenib tosylate polymorphic form I analyzed according to Reference Example 1 e). On the x axis, the Raman shift/cm−1 is shown with explicit values of 500, 1000, 1500, and 2000. On the y axis, the counts are shown with explicit values of from 10000 to 70000.

Further, the obtained crystalline compound was characterized by Raman spectroscopy as described in Reference Example 1 e). The following peak table (Table 4) was obtained. The Raman spectrum is shown in FIG. 4.

TABLE 4

Raman spectrum peak table polymorph form I

| Raman shift [cm$^{-1}$] | Intensity | Relative Intensity |
|---|---|---|
| 1724 | 3000 | 5.5 |
| 1688 | 7000 | 12.7 |
| 1630 | 4000 | 7.3 |
| 1612 | 6000 | 10.9 |
| 1601 | 7000 | 12.7 |

TABLE 4-continued

Raman spectrum peak table polymorph form I

| Raman shift [cm$^{-1}$] | Intensity | Relative Intensity |
|---|---|---|
| 1420 | 3000 | 5.5 |
| 1325 | 25000 | 45.5 |
| 1310 | 10000 | 18.2 |
| 1278 | 5000 | 9.1 |
| 1268 | 7000 | 12.7 |
| 1212 | 7000 | 12.7 |
| 1163 | 12000 | 21.8 |
| 1134 | 10000 | 18.2 |
| 1117 | 22000 | 40.0 |
| 1033 | 25000 | 45.5 |
| 1011 | 55000 | 100.0 |
| 922 | 8500 | 15.5 |
| 863 | 12000 | 21.8 |
| 825 | 17000 | 30.9 |
| 803 | 29000 | 52.7 |
| 791 | 9000 | 16.4 |
| 751 | 8000 | 14.5 |
| 724 | 2500 | 4.5 |
| 685 | 12000 | 21.8 |
| 639 | 6500 | 11.8 |
| 582 | 3200 | 5.8 |
| 566 | 3400 | 6.2 |
| 555 | 4800 | 8.7 |
| 516 | 2000 | 3.6 |
| 496 | 3100 | 5.6 |
| 450 | 1950 | 3.5 |
| 427 | 2000 | 3.6 |

Example 1

A tablet was prepared based on the following starting materials:

Granulate:

| | |
|---|---|
| Sorafenib tosylate form III | 274.0 mg |
| Cellulose microcristalline | 16.0 mg |
| Crosscarmellose Na (Ac-Di-Sol) | 15.3 mg |
| Hypromellose 5 cP | 10.2 mg |
| Sodium dodecyl sulphate | 1.7 mg |
| (Water | 317.2 mg) |

Outer Phase:

| | |
|---|---|
| Magnesium stearate | 1.7 mg |
| Crosscarmellose Na (Ac-Di-Sol) | 21.1 mg |

All solid ingredients of the granulate without sodium dodecyl sulphate were blended and granulated by mixing with a solution of sodium dodecyl sulphate in water. This was done manually in a small scale with a mortar and a pistil. The damp mass was passed through a sieve to form a granulate. A prescription sieve with 1.5 mm mesh size was used. After tray drying, the granulate was blended with the excipients of the outer phase as given above using a free-fall blender and compressed to tablets using a hydraulic press. The tablets had a diameter of 10 mm and were pressed at about 6 kN.

The tablets were tested according to Reference Example 1 d) and were found to contain sorafenib tosylate form III; no sorafenib tosylate form I could be detected. Dissolution testing of the tablets according to the method described in reference example 1 b) reveals a drug portion of 45% dissolved after 5 min and 92% after 15 min.

The thus obtained tablets were double sealed in polyethylene film (each layer 60 micrometer), stored according to Reference Example 1 a) and, after storing, subjected to a dissolution test as described in Reference Example b). Dissolution testing of the tablets after storage according to the method described in Reference Example 1 b) reveals a drug portion of 12% dissolved after 5 min and 82% after 15 min.

Comparative Example 1

A tablet was prepared based on the following starting materials:

Granulate:

| | |
|---|---|
| Sorafenib tosylate form I | 274.0 mg |
| Cellulose microcristalline | 16.0 mg |
| Crosscarmellose Na (Ac-Di-Sol) | 15.3 mg |
| Hypromellose 5 cP | 10.2 mg |
| Sodium dodecyl sulphate | 1.7 mg |
| (Water | 317.2 mg) |

Outer Phase:

| | |
|---|---|
| Magnesium stearate | 1.7 mg |
| Crosscarmellose Na (Ac-Di-Sol) | 21.1 mg |

All solid ingredients of the granulate without sodium dodecyl sulphate were blended and granulated by mixing with a solution of sodium dodecyl sulphate in water. This was done with a mortar and a pistil. The damp mass was passed through a sieve to form a granulate. A prescription sieve with 1.5 mm mesh size was used. After tray drying, the granulate was blended with the excipients of the outer phase using a free-fall blender and compressed to tablets in a hydraulic press. The tablets had a diameter of 10 mm and were pressed at about 6 kN.

Dissolution testing of the tablets according to the method described in Reference Example 1 b) reveals a drug portion of 69% dissolved after 5 min and 100% after 15 min.

Comparative Example 2

Commercial tablets of Nexavar®, having a composition of the tablet core identical to that of the tablets of Comparative Example 1, have been tested according to the method described in reference example 1 b), revealing a drug portion of 42% dissolved after 5 minutes and of 95% after 15 minutes.

The tablets were then packaged in a polypropylene blister (300 micrometer) with an aluminium push-through foil (20 micrometer) and stored according to Reference Example 1 a). Dissolution testing of the tablets after storage according to the method described in reference example 1 b) reveals a drug portion of 0% dissolved after 5 min and 28% after 15 min.

Example 2

A tablet was prepared based on the following starting materials:

Granulate:

| | |
|---|---|
| Sorafenib tosylate form III | 274.0 mg |
| Cellulose microcristalline | 16.0 mg |
| Crosscarmellose Na (Ac-Di-Sol) | 15.3 mg |
| Hypromellose 5 cP | 10.2 mg |
| Sodium dodecyl sulphate | 1.7 mg |
| (Water | 317.2 mg) |

Outer Phase:

| Magnesium stearate | 1.7 mg |
|---|---|
| Crosscarmellose Na (Ac-Di-Sol) | 21.1 mg |
| Cellulose microcrystalline | 340.0 mg |

An solid ingredients of the granulate without sodium dodecyl sulphate were blended and granulated by mixing with a solution of sodium dodecyl sulphate in water. This was done with a mortar and a pistil. The damp mass was passed through a sieve to form a granulate. A prescription sieve with 1.5 mm mesh size was used. After tray drying, the granulate was blended with the excipients of the outer phase using a free-fall blender and compressed to tablets in a hydraulic press. The tablets had a diameter of 13 mm and were pressed at about 6 kN.

The tablets were tested according to Reference Example 1 d) and were found to contain sorafenib tosylate form III; no sorafenib tosylate form I could be detected. Dissolution testing of the tablets according to the method described in Reference Example 1 b) reveals a drug portion of 89% dissolved after 5 min and 99% after 15 min.

Example 3

A dispersible tablet was prepared based on the following starting materials:
Granulate:

| Sorafenib tosylate form III | 274.0 mg |
|---|---|
| Mannitol | 274.0 mg |
| (Water | 182.6 mg) |

Outer Phase:

| Cellulose microcrystalline | 27.6 mg |
|---|---|
| Sodium starch glycolate | 27.6 mg |

All solid ingredients of the granulate were blended and granulated by mixing with water. This was done with a mortar and a pistil. The damp mass was passed through a sieve to form a granulate. A prescription sieve with 1.5 mm mesh size was used. After tray drying, the granulate was blended with the excipients of the outer phase using a free-fall blender and compressed to tablets in experiments a hydraulic press. The tablets had a diameter of 10 mm and were pressed at about 6 kN.

The tablets were tested according to Reference Example 1 d) and were found to contain sorafenib tosylate form III; no sorafenib tosylate form I could be detected. Dissolution testing of the granulate according to the method described in example 4 reveals a drug portion of 95% dissolved after 5 min and 100% after 15 min. Tablets pressed from this granulate disintegrated in a glass of water at room temperature completely within a few minutes.

Example 4

A dispersible tablet was prepared based on the following starting materials:
Granulate:

| Sorafenib tosylate form III | 274.0 mg |
|---|---|
| Mannitol | 274.0 mg |
| Lecithin | 13.7 mg |
| (Water | 123.3 mg) |

Outer Phase:

| Cellulose microcrystalline | 28.1 mg |
|---|---|
| Sodium starch glycolate | 28.1 mg |

All solid ingredients of the granulate without lecithin were blended and granulated by mixing with a solution of lecithin in water. This was done with a mortar and a pistil. The damp mass was passed through a sieve to form a granulate. A prescription sieve with 1.5 mm mesh size was used. Dissolution testing of the granulate according to the method described in Reference Example 1 b) reveals a drug portion of 100% dissolved after 5 min.

After tray drying, the granulate was blended with the excipients of the outer phase using a free-fall blender and compressed to tablets in a hydraulic press. The tablets had a diameter of 10 mm and were pressed at about 6 kN.

The tablets were tested according to Reference Example 1 d) and were found to contain sorafenib tosylate form III; no sorafenib tosylate form I could be detected. Dissolution testing of the tablet according to the method described in Reference Example 1 b) reveals a drug portion of 90% dissolved after 5 min and 93% after 15 min. In a glass of water at room temperature the tablets completely disintegrated within a few minutes.

LITERATURE CITED

WO 00/42012
WO 2006/034797
WO 2006/094626
WO 2009/092070

The invention claimed is:

1. An oral solid dosage form, comprising a crystalline sorafenib tosylate characterized by an X-ray powder diffraction pattern showing peak maxima at 2 theta/° values of 7.7±0.2, 12.0±0.2, 19.9±0.2, and 21.6±0.2, the X-ray powder diffraction pattern being determined at a temperature of about 22° C. using copper-Kalpha1/2 radiation having a wavelength of 0.15419 nm, and at least one excipient.

2. The dosage form of claim 1, comprising a crystalline sorafenib tosylate characterized by a Raman spectrum showing peak maxima at Raman shift/cm$^{-1}$ values of 1715±5, 1601±5, 1334±5, 1268±5, 1033±5, and 1011±5, the Raman spectrum being determined using a laser having a wavelength of 532 nm wherein the exposure time of the sample is 2 s, and at least one excipient.

3. The dosage form according to claim 1, comprising at least 90% by weight, relative to the total amount of sorafenib tosylate, of the crystalline sorafenib tosylate according to claim 1.

4. The dosage form of claim 1, comprising at most 5% by weight, relative to the crystalline sorafenib tosylate according to claim 1, of a crystalline sorafenib tosylate characterized by an X-ray powder diffraction pattern showing peak maxima at 2 theta/° values of 4.3±0.2, 11.0±0.2, 14.8±0.2, 17.9±0.2, 19.3±0.2, 20.5±0.2 and 20.8±0.2, 21.5±0.2, 22.9±0.2, 24.5±0.2, the X-ray powder diffraction pattern being determined at a temperature of about 22° C. using copper-Kalpha1/2 radiation having a wavelength of 0.15419 nm, and/or of a crystalline sorafenib tosylate characterized by a Raman spectrum showing peak maxima at Raman shift/cm$^{-1}$ values of 1688±5, 1612±5, 1601±5, 1325±5, 1310±5, 1268±5, 1212±5, 1163±5, 1117±5, 1033±5, 1011±5, 922±5, 863±5, 825±5, 803±5, 791±5, 751±5, 685±5, 639±5, the Raman spectrum being determined using a laser having a wavelength of 532 nm wherein the exposure time of the sample is 2 s.

5. The dosage form of claim 1, comprising crystalline sorafenib tosylate according to claim 1 in an amount of at least 40% by weight relative to the total weight of the oral dosage form.

6. The dosage form of claim 1 being a compressed dosage form.

7. The dosage form of claim 1 comprising at least one filler in an amount of from 2 to 55% by weight, at least one disintegrant in an amount of from 4 to 12% by weight, at least one binder in an amount of from 0.25 to 8% by weight, at least one lubricant in an amount of from 0.1 to 1.0% by weight and at least one surfactant in an amount of from 0.1 to 1.0% by weight in each case relative to the total weight of the oral dosage form.

8. The dosage form of claim 7 wherein the at least one filler is microcrystalline cellulose, wherein the at least one disintegrant is croscaramellose, wherein the at least one binder is hypromellose, wherein the at least one lubricant is magnesium stearate and wherein the at least one surfactant is sodium lauryl sulfate.

9. The dosage form of claim 1 being a dispersable tablet or granule, said oral dosage form comprising at least one first filler selected from the group consisting of sugars, sugar alcohols, oligosaccharides, pharmaceutically acceptable polyvinyl derivatives, pharmaceutically acceptable polyalkylene glycols, and mixtures of two or more thereof in an amount of from 5 to 55% by weight, at least one second filler in an amount of from 1 to 10% by weight, at least one disintegrant in an amount of from 1 to 10% by weight, and optionally of from 1 to 5% by weight of a surfactant, said oral dosage form comprising less than 0.1% by weight of sodium lauryl sulfate, in each case relative to the total weight of the oral dosage form.

10. The dosage form of claim 9, comprising less than 0.1% by weight of a surfactant.

11. A method for the preparation of an oral solid dosage form according to claim 1 said method comprising
   a) providing a crystalline sorafenib tosylate according to claim 1;
   b) mixing the crystalline sorafenib tosylate provided in a) with at least one excipient;
   c) preparing the oral solid dosage form based on the mixture obtained in b).

12. A method of treating mammalian hyper-proliferate disorders said disorder optionally being renal cell carcinoma or hepatocellular carcinoma comprising administering the oral solid dosage form of claim 1.

13. The method of claim 12, wherein the oral solid dosage form is to be administered to patients in a country having an area with an Af or an Am climate according to the Köppen-Geiger climate classification.

14. A method for the preparation of an oral solid dosage form using a crystalline sorafenib tosylate of claim 1 wherein said oral solid dosage form has an increased dissolution rate after packaging in a polyethylene film and storing in the dark at 40° C. at a relative humidity of 75% for a period of at least 14 days, compared to an identically packaged and stored oral solid dosage form comprising, instead of said crystalline sorafenib tosylate, a crystalline sorafenib tosylate characterized by an X-ray powder diffraction pattern showing peak maxima at 2 theta/° values of 4.3±0.2, 11.0±0.2, 14.8±0.2, 17.9±0.2, 19.3±0.2, 20.5±0.2 and 20.8±0.2, 21.5±0.2, 22.9±0.2, 24.5±0.2, the X-ray powder diffraction pattern being determined at a temperature of about 22° C. using copper-Kalpha1/2 radiation having a wavelength of 0.15419 nm, and/or of a crystalline sorafenib tosylate characterized by a Raman spectrum showing peak maxima at Raman shift/cm$^{-1}$ values of 1688±5, 1612±5, 1601±5, 1325±5, 1310±5, 1268±5, 1212±5, 1163±5, 1117±5, 1033±5, 1011±5, 922±5, 863±5, 825±5, 803±5, 791±5, 751±5, 685±5, 639±5, the Raman spectrum being determined using a laser having a wavelength of 532 nm wherein the exposure time of the sample is 2 s, wherein the dissolution rate is determined using an USP 2 apparatus with a stirrer speed of 75 rpm, a test temperature of 37° C. and as dissolution medium 900 ml of a 0.1 N HCl solution with 1% sodium dodecyl sulphate.

15. A pharmaceutical composition comprising the crystalline sorafenib tosylate of claim 1, wherein said pharmaceutical composition is packaged in a packaging material having a moisture vapour transmission rate of at least 0.4 g m$^{-2}$ d$^{-1}$ as measured according to standard DIN 53122-1.

\* \* \* \* \*